United States Patent [19]
Rodgers et al.

[11] Patent Number: 5,404,762
[45] Date of Patent: Apr. 11, 1995

[54] QUICK-CHANGE FILTER CARTRIDGE

[75] Inventors: John C. Rodgers, Santa Fe, N. Mex.; Andrew R. McFarland, College Station; Carlos A. Ortiz, Bryan, both of Tex.

[73] Assignee: The Regents of the Univ. of California Office of Technology Transfer, Alameda, Calif.

[21] Appl. No.: 3,990

[22] Filed: Jan. 15, 1993

[51] Int. Cl.⁶ .............................................. G01N 1/00
[52] U.S. Cl. .................................................. 73/863.25
[58] Field of Search ........................ 73/863.21–863.25, 73/28.04; 55/270, 356, 482, 485, 490, 494, 495, 501–504, DIG. 9

[56] References Cited

U.S. PATENT DOCUMENTS

| | | | |
|---|---|---|---|
| 2,035,097 | 3/1936 | Schwartz | 55/501 |
| 3,505,794 | 4/1970 | Nutter et al. | 55/502 |
| 4,155,247 | 5/1979 | Kaczmarek et al. | 73/863.21 |
| 4,350,037 | 9/1982 | Higham | 73/863.21 |
| 5,223,439 | 6/1993 | Rolle | 73/28.04 |

OTHER PUBLICATIONS

Andrew R. McFarland et al., "Continuous Air Monitor for Alpha–Emitting Aerosol Particles," in Proceedings of the 21st DOE/NRC Nuclear Air Cleaning Conference, Sessions 9–16, M. W. First, Ed. (San Diego, Calif., Aug. 13–16, 1990), NUREG/CP–0116, CONF–900813, vol. 2, pp. 859–871.

*Primary Examiner*—Robert Raevis
*Attorney, Agent, or Firm*—Samuel M. Freund

[57] ABSTRACT

A quick-change filter cartridge. In sampling systems for measurement of airborne materials, a filter element is introduced into the sampled airstream such that the aerosol constituents are removed and deposited on the filter. Fragile sampling media often require support in order to prevent rupture during sampling, and careful mounting and sealing to prevent misalignment, tearing, or creasing which would allow the sampled air to bypass the filter. Additionally, handling of filter elements may introduce cross-contamination or exposure of operators to toxic materials. Moreover, it is desirable to enable the preloading of filter media into quick-change cartridges in clean laboratory environments, thereby simplifying and expediting the filter-changing process in the field. The quick-change filter cartridge of the present invention permits the application of a variety of filter media in many types of instruments and may also be used in automated systems. The cartridge includes a base through which a vacuum can be applied to draw air through the filter medium which is located on a porous filter support and held there by means of a cap which forms an airtight seal with the base. The base is also adapted for receiving absorbing media so that both particulates and gas-phase samples may be trapped for investigation, the latter downstream of the aerosol filter.

4 Claims, 4 Drawing Sheets

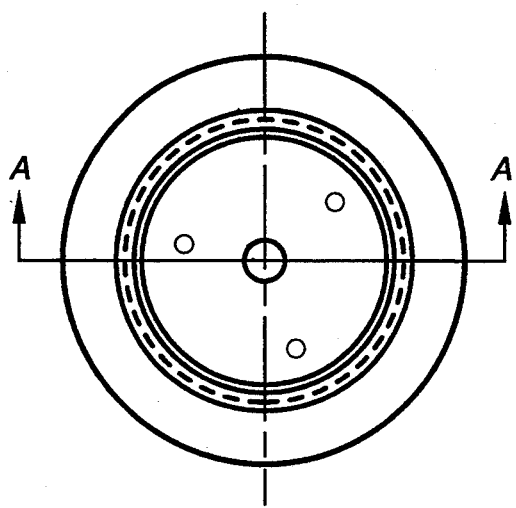
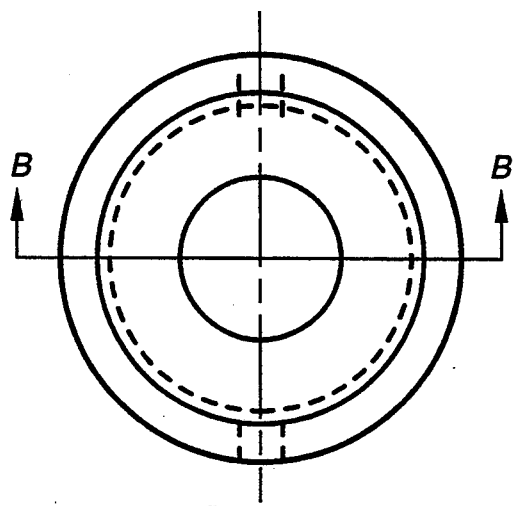
Fig. 1a1    Fig. 1b1
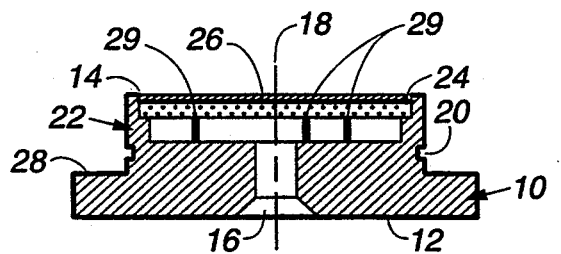
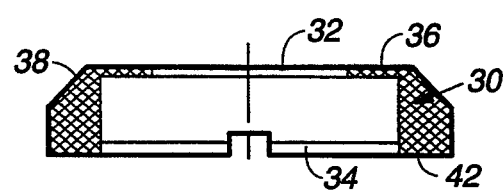
Fig. 1a    Fig. 1b
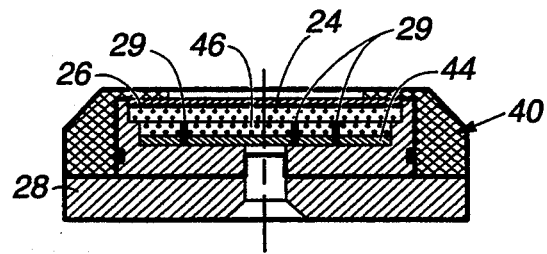
Fig. 1c

QUICK-CHANGE FILTER CARTRIDGE

BACKGROUND OF THE INVENTION

The present invention relates generally to aerosol and certain gaseous element filters and samplers and, more particularly, to filter-holding apparatus which permits the filter to be preloaded, and thereby readily changed, and which will allow vapor-phase materials to be sampled simultaneously with particulates. This invention was made with government support under Contract No. W-7405-ENG-36 awarded by the U.S. Department of Energy. The government has certain rights in the invention.

A variety of sampling instrumentation exists for extracting a sample of airborne materials for measurement. Common among such instrumentation is the requirement for introducing a filter element in the sampled airstream such that the aerosol and vapor-phase constituents are removed and deposited on the filter or captured in an absorber. In many applications, the physical characteristics of the filter medium are critical to the success of the sampling process (i.e., pore size, physical structure, chemical formulation, etc.). Sampling media are frequently fragile, requiring mechanical support during the sampling process sufficient to prevent rupture due to the large pressure differences generated by the sampling pump, and requiring careful mounting and sealing to prevent misalignment, tearing, or creasing which could allow sampled air to bypass the filter altogether. Other concerns arise from operator handling of filters in the field during the exchange process, such as cross-contamination of samples or exposure of the operator to toxic materials. The requirement for careful mounting of some filter media leads to increased operator time to complete filter exchange, and difficulties achieving automation of the filter exchange process.

Continuous air monitoring (CAM) instrumentation is widely used in the nuclear industry to monitor and detect the presence of radioactivity in workplace air and stack-discharge air. Typically, CAM devices monitoring for particulate radioactivity in air collect aerosol particles on a substrate medium, which is a filter through which the continuous sample is drawn. Radioactive emissions from the collected sample are detected by a planar detection device (solid state or gas-filled chamber) placed parallel to the collector surface and separated by a small gap through which the air sample must pass.

There are several aspects of the alignment of the sample filter, the sample flow path, and the detector-filter gap space, which affect the performance of the CAM instrument, especially in the situation where the accurate determination of the energy of the radioactive emissions from the sample is critical to the detection and alarm functions. First, the filter medium must be consistently and accurately positioned in line with the detector. Failure to accurately and repeatably position the sample-collection surface with respect to the detector can result in changing geometry for radiation detection, thereby affecting detection efficiency. Moreover, loss in energy discrimination due to differing energy absorption from sample to sample may also occur. Second, the design of the flow path from the CAM inlet to the filter can affect the quantity of the sample lost on the internal surfaces of the CAM head. If these deposits occur in positions from which irradiation of the detector can occur, spurious signals can result, leading to inaccurate measurements or false alarms. Hence, sample flow path can affect both the sampling efficiency and accuracy of the instrument. These undesirable deposits can also contaminate the filter-holding assemblies resulting in possible subsequent contamination of the operator, and possible cross-contamination between samples. Third, the gap between the filter surface and the detector must be repeatably and accurately maintained to ensure accurate energy determination and efficiency.

In addition to repeatable, accurate radiation detection, there are several additional CAM head design considerations related to the filter-holding and positioning mechanisms which are critical. First, since many filter media are fragile, the method of mounting the filter in a holder must not result in a twisting or tearing of the medium as closure is achieved. Moreover, the seal must be sufficiently tight and positive that leaks around edges and joints which would allow a portion of the sampled air volume to bypass the filter do not occur. Second, the filter-exchange process should be ergonomically efficient so that a manual change of filter can be reliably and rapidly made. There should be a minimum of wasted motion and possibilities for inadvertent loss of the samples, or cross-contamination. Mechanical assembly/disassembly associated with the filter-change process should not cause rapid wear of instrument components or surfaces leading to premature failure or frequent service and repair.

In the past, a distinction has been drawn between the interpretation of the results of CAM sampling and fixed-air sampling (FAS). This is because it was assumed that the sample obtained by a CAM is not representative of the size distribution of the contaminant aerosol, and therefore, of the concentration near the point of release, due to the sampling characteristics of the CAM inlet (and sampling line), and to the placement of the CAM. The FAS sampler, by contrast, is generally placed closer to potential release points, and has no sampling inlet bias. With the development of more recent CAM technology, this distinction is not as clearly justified as it once was. Furthermore, modern CAM heads have the capability of being located remotely from the data processing and display unit.

All CAMs must have means for introducing a sample collection medium (filter) into, and removing it from, the sample airstream adjacent to a detector. The short range of some of the radiations of interest in CAM applications dictates that the filter be placed in close proximity to the detector, so that during the filter-exchange procedure, the detector and filter must be moved apart such that the filter holder can be opened and a replacement filter installed. A "clam-shell" design, which was found in some early CAM designs, allows the filter holder to be rotated away from the detector while maintaining the vacuum connection to the holder. All elements of the filter-holding apparatus remain attached to the instrument. A disadvantage of this design is that the aerosol-flow pattern in the "clam-shell" tends to impinge upon the holder, thereby resulting in inadvertent aerosol loss and contamination of extraneous surfaces. Moreover, the precut filter medium itself must be carefully handled by the operator during the filter-change procedure in order to avoid damage and cross-contamination. Other designs permit the complete removal of the filter-holding apparatus from the CAM head during filter change. While this can simplify the filter-handling operation, it can create another difficulty, since now the filter holder is separated from the vacuum source, which connection must be reestablished. One manufacturer uses a drawer to move a filter in and out of their alpha-emitter particulate CAM head. Aerosol enters the head through a large-diameter entrance nozzle and is directed into the aerosol-inlet plenum which surrounds both the filter holder in the drawer and the detector, thereby being exposed to extraneous surfaces in its path to the filter. The entire aerosol-inlet plenum is at negative pressure (a vacuum) relative to ambient pressure, necessitating a vacuum seal at both the interface with the vacuum connection at the base of the drawer, and the outside case of the head near the drawer handle. In the former instance, the seal is required to be a sliding seal, subject to wear and tear. The filter is held in place on the drawer with a "filter ring holder", a thin steel ring, which clamps the filter down by action of a magnet in the drawer. Change of filter in the ring-and-magnet case is difficult and time-consuming, and is subject to cross-contamination due to the requirement for handling, removing, and replacing the filter medium and the ring holder.

Accordingly, it is an object of the present invention to provide a filter cartridge which gives sufficient support to the filter material such that rupture thereof is prevented as a result of pressure differentials applied thereto.

Another object of the present invention is to provide an aerosol filter, or a combination aerosol filter and absorber, cartridge which permits accurate alignment of the filter with a detector and long-term reliable sealing of the cartridge/filter medium combination so that sampled gas cannot bypass the filter.

Yet another object of the invention is to provide a filter cartridge which reduces operator exposure to dangerous materials deposited on the filter cartridge and filter medium and cross-contamination thereof by the operator.

Still another object of the present invention is to provide a simple, low-cost filter cartridge which can be preloaded by the operator with a fresh filter medium, under controlled laboratory conditions, so that the filter changing procedure in the field involves replacement of the filter cartridge. This is in place of replacing the filter medium itself, and is adaptable to automatic introduction and removal from air sampling devices.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the filter cartridge of this invention may include in combination: a porous, solid, short, right-cylindrical, filter-support member having two flat, parallel sides upon one of which the aerosol filter is placed; a right-cylindrical, base member having a flat closed end and an open end parallel thereto, the closed end thereof having a tapered hole therethrough aligned with the cylindrical axis for applying vacuum to the filter cartridge, the outside wall of the cylindrical portion of the base having an O-ring groove, and the inside wall thereof having a shelf for holding the filter-support member perpendicular to the cylindrical axis and substantially flush with the open end of the base, thereby defining a volume between the filter-support member and the closed end of the base into which an absorber medium can be introduced if desired, the base further having a flange coextensive with the closed end thereof; an O-ring having the appropriate dimensions to fit into the groove therefor in the outside wall of the base; and a right-cylindrical cap having two open ends and a diameter larger than the base such that the cap slides over the base, and the O-ring forms a gas-tight seal between the outside wall of the base and the inside wall of the cap member, the cap further having a circular lip reducing the diameter of one open end thereof such that the filter is held in place when the cap member is compressed against the base, but is not crushed since the other open end of the cap contacts the flanged end of the base.

Benefits and advantages of the present invention include support for fragile sampling media in order to prevent rupture during sampling; simplified filter medium mounting and sealing which prevents misalignment, tearing, or creasing which would allow the sampled air to bypass the filter; reduction of cross-contamination of the filter media and operator exposure to toxic materials, since the filter material need not be handled directly during the filter-exchange process; the ability to preload the filter medium into the filter cartridge in the laboratory prior to filter exchange in the field; and the application to a wide variety of filter media to many types of instruments, including automated systems and systems designed to monitor for contaminants present in volatile form.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIGS. 1a–1c, 1a1 (top view) and 1b1 (top view) are a schematic representating the filter cartridge of the present invention. FIG. 1a illustrates the cylindrical base member; FIG. 1b illustrates the cylindrical cap member; and FIG. 1c illustrates the assembled apparatus.

DETAILED DESCRIPTION OF THE INVENTION

Figure 2:
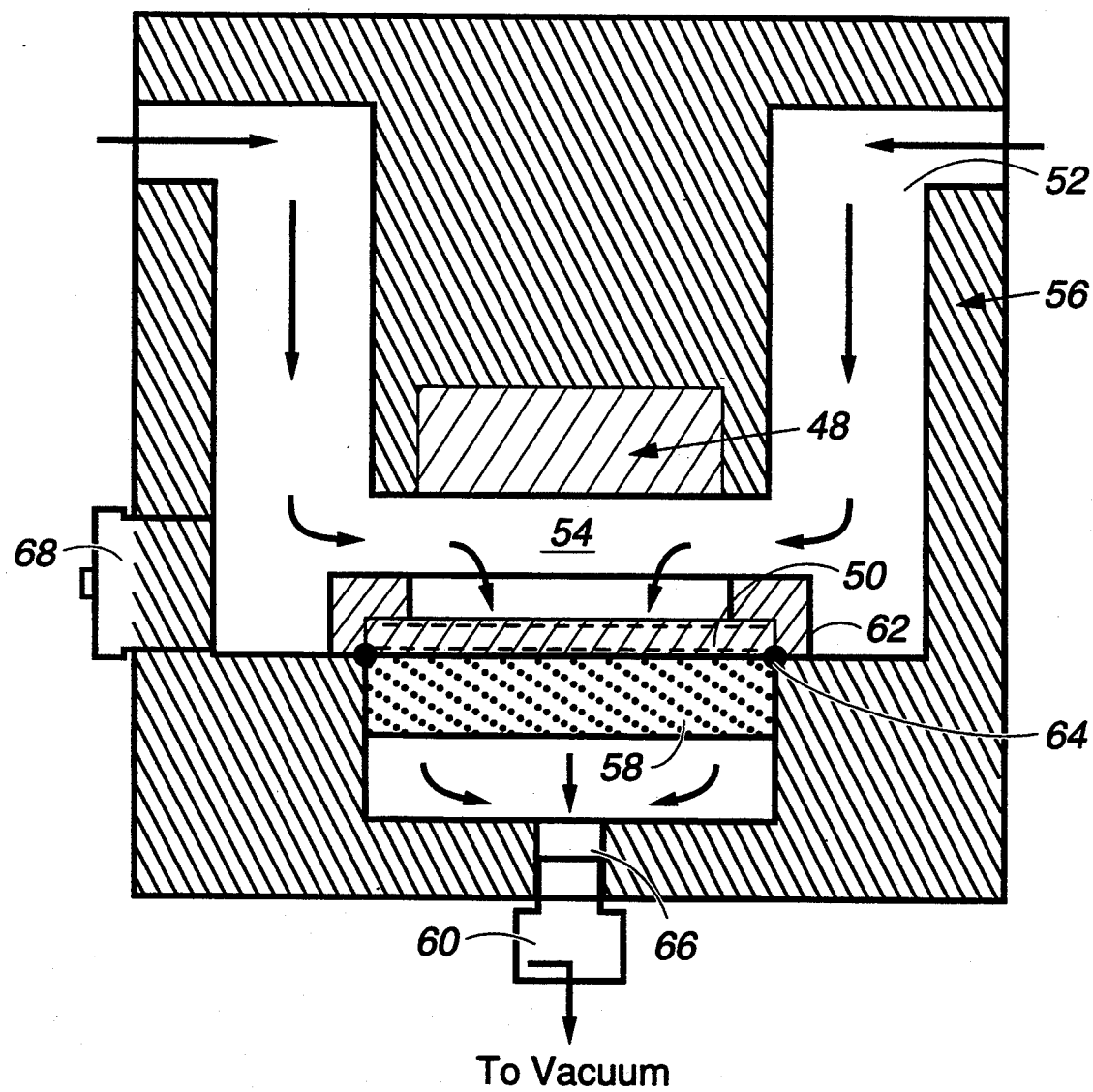
FIG. 2 is a schematic representation of a typical CAM sample collection and counting apparatus.

Briefly, the present invention includes a quick-change filter cartridge which resolves many of the problems associated with utilizing a wide range of filter media in many types of instruments, and which readily lends itself to automatic filter change.

Reference will now be made in detail to the present preferred embodiments of the invention, examples of which are illustrated in the accompanying drawings.

The same or similar structure in the drawings is identified in what follows by the same callouts.

Turning now to FIG. 1, the components of the filter cartridge of the present invention are illustrated. FIG. 1a shows a cylindrical base member 10 having a flat, closed end 12 and an open end 14 parallel thereto, the closed end thereof having a tapered hole 16 therethrough aligned with the cylindrical axis 18 of the base for applying vacuum to the filter holder, the outside wall of the cylindrical portion of the base having an O-ring groove 20, and the inside wall thereof having a circular shelf 22 for holding a filter-support member 24 perpendicular to axis 18 and approximately flush with open end 14. Filter-support member 24 is a porous, solid wafer having two flat, parallel sides upon one of which filter medium 26 is placed. Base 10 further has a flange 28 coextensive with closed end 12. Posts 29 may be added to base 10 if additional support for the filter-support member is required.

FIG. 1b shows a cylindrical cap member 30 having two open ends 32 and 34, and a diameter larger than base 10 such that cap 30 slides over base 10, and an O-ring which is situated in O-ring groove 20 forms a gas-tight seal between the outside wall of base 10 and the inside wall of cap 30. The cap also has a circular lip 36 which reduces the diameter of open end 32 such that filter medium 26 is held in place when cap member 30 is compressed against base member 10. Cap member 30 has a circular, tapered portion 38 contiguous with circular lip 36 such that the aerosol filter holder may be reversibly located in an air-sampling apparatus.

FIG. 1c shows the assembled filter cartridge 40. Filter 26 is not crushed when base 10 and cap 30 are pressed together since the terminus 42 of the wall of cap 30 at open end 34 contacts the flanged portion 28 of base 10.

In certain applications where the radioactive species can exist in both particulate and vapor form, such as in the case of radioiodine, the form of the quick-change cartridge readily accommodates the introduction of an absorbent material such as activated charcoal into the volume behind the filter-medium support element. In such applications, a screen, 44, can be utilized to retain the absorbent material in volume 46 within the cartridge. The absorbent material may also be used to remove toxic materials from the sampled air. Thus, the present filter cartridge is capable of extracting particulate materials for detection and counting purposes. Such materials would be captured by the precut filter medium. Moreover, any volatile or gaseous constituents which can be trapped by a suitable absorbing medium, and which would otherwise pass through the particulate filter medium and not be detected, may now be counted.

In use, the cap member is removed by sliding it off of the base, a piece of filter material is positioned on the filter support, and the cap is then pushed down onto the base, where it secures the filter in place and seals it by action of the O-ring and pressure between flange 36 in the cap and the filter-support member 26. A 0.030 in. lip was found to be sufficient to hold the filter in place. Vacuum is applied to the filter through the sampling port which is drilled coaxially through the base. The present filter cartridge gives rise to ease and rapidity of filter exchange, while at the same time the potential for filter damage and bypass leakage are minimized. A most important feature of the cartridge, however, is that the external parts of the assembly are completely outside of the incoming sample airflow path. Essentially the only surface exposed to the incoming sample is the filter medium itself. As a result, no opportunity for inadvertent sample deposit is present. The small size of the cartridge, and the fact that it can be completely removed from the CAM head along with the filter backplane allows the operator to have preloaded cartridges ready to feed into the CAM by either manual or automated means. Each cartridge could have a unique identifier tag, e.g., a barcode, which would provide a convenient chain-of-custody mechanism for the filter and data obtained from it. The barcode could be updated at the time each cartridge is preloaded in the laboratory prior to the field-exchange process, and at the time of loading the CAM head, by hand or automatically.

As an example of the use of the aerosol filter cartridge of the present invention, sample collection and energy-specific radionuclide determination, especially of alpha-emitting radionuclides which have very short ranges in solids and air, in a continuous air monitoring instrument will be described.

A generalized schematic of a CAM sample collection and counting apparatus is shown in FIG. 2. Planar detector means 48 (e.g., for alpha-particle detection, a solid-state, silicon-junction diode would be employed) is positioned coaxially and spaced precisely above planar filter medium 50. A sample is collected on filter medium 50 by drawing an air sample along path 52 into air gap 54 through filter medium 50 by means of a vacuum applied to the underside of the filter. Isotropic ionizing radiation emissions from the sample on the filter pass through air gap 54 to detector means 48 where they deposit their remaining energy which is registered as an electrical signal containing energy information in a spectrometer device (not shown). To initiate the sampling and counting cycle, the filter medium 50 must be introduced into the CAM body 56 in such a way that it is accurately positioned, both with respect to detector means 48 and filter backplane 58, to which the vacuum of the sampling line 60 is applied during sampling. In the process of introducing filter medium 50 into the CAM and positioning it on the filter backplane 58, a vacuum seal must be established between filter medium 50 and backplane 58. This is to prevent airflow around the filter medium, which would introduce an error in the determination of radioactivity concentration (activity per unit volume) in the air sample. The filter seal is typically achieved using a filter cap 62 and an O-ring 64, or a similar seal arrangement. The filter backplane 58 must be designed such that it retains a planar configuration during the sample collection process even under severe downward forces (toward backplane 58) which develop as vacuum is applied to porous filter medium 50. If the surface deforms, distortions in counting geometry result which cause loss of energy resolution and detector efficiency. Unlike the design of the present invention, in the typical CAM instrument, the filter backplane 58, the CAM vacuum connection and seal 66, and sampling line (vacuum source) 60, are either partially or altogether permanent fixtures of CAM body 56, or are attached to this body. With such a standard CAM filter handling design, during each cycle of sampling and counting, the CAM body 56 must be opened (sometimes through a filter change port 68) to allow filter medium 50 to be manually affixed to backplane 58, and manually sealed to it by filter cap 62 and seal 64, before being exposed to the airflow. In such CAM instruments, as a result of design requirements for achieving access to the filter in its mounting, the filter changing apparatus and its support structures and the filter cap and seal, remain in the sample flow path along with the filter during the sampling process. In the present invention, this problem is eliminated.

Although a number of variations exist in the apparatus described in FIG. 2, the identified features are descriptive of typical CAM instrumentation currently in use. The present invention achieves the requirements for accurate, repeatable counting geometry, and secure, reliable vacuum sealing, and has the advantage of preloading of a quick-change cartridge. At the same time, the filter mounting assembly is sheltered from continuous exposure to airstream contaminants, and offers the possibility for automation of what heretofore has been a manual filter-change process when precut disk filter media are involved.

Figure 3:
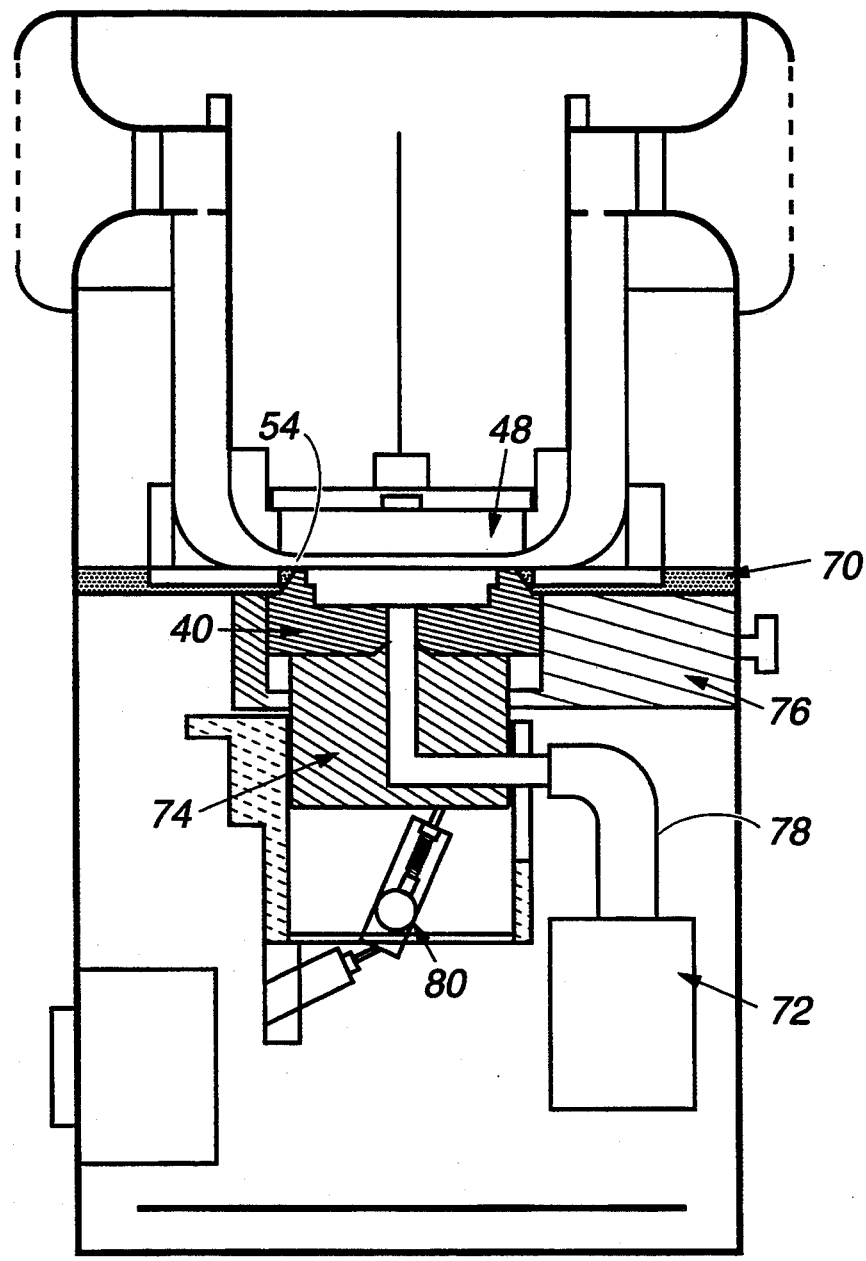
FIG. 3 is a schematic representation of a CAM sampler head fitted with the filter cartridge of the present invention.

A CAM sampler head fitted with the quick-change filter cartridge of the present invention is schematically illustrated in FIG. 3 in the configuration for manual filter exchange with a filter change drawer. Shown is detector means 48 positioned above the filter which is mounted in the filter holder 40. Cover plate 70 mates precisely with filter holder 40 in the closed position, which assures positive positioning and constant gap 54. Note particularly that filter cartridge 40 and the filter changing drawer 76 are entirely outside of the flow path of the air sample from inlet to impingement on the filter surface. Thus, there is no possibility for the deposit of sample aerosol on extraneous surfaces of the filter cartridge or drawer. Filter holder 40 is simultaneously connected to a vacuum source 72 which draws air through the CAM sampler and pushed upward into place against cover plate 70 by piston means 74. An O-ring on the face of the piston assures a positive, non-rotating vacuum seal to the filter cartridge base. The piston assembly, when in its full retracted position, allows the quick-change filter cartridge to move down away from cover plate 70 and be retained in filter drawer 76, where it can be easily and rapidly removed for a change of filters. Note that in the retracted position the piston is positioned entirely outside the drawer assembly, allowing the drawer to be readily removed. Flexible vacuum hose 78 facilitates this operation. A quarter-turn device 80 is used to move the piston up and down. A CAM sampler head fitted with an automated quick-change cartridge changer can be similarly employed; for example, a lazy-susan wheel or a cartridge loader may be utilized for this purpose. A feature of the present quick-change filter cartridge is that all of the mechanical compression and vacuum sealing of the filter medium into position against the backplane is achieved with the cap and base components. Any required vacuum seals at the base and top of the cartridge for purposes of achieving air flow through the filter medium itself are made against flat cartridge surfaces, not against the filter medium itself. As a result, no part of the drawer cartridge handling element of the CAM is required to make a vacuum-tight or air-tight seal with any other surfaces of the CAM of the present invention, as in other designs. Thus, wear by sliding friction during insertion and removal will not contribute to loss of performance due to leakage in the sampling line.

In the present quick-change filter cartridge, isolation of the filter cartridge and sample-changing apparatus from the incoming sample airstream is accomplished by the removal of the porous filter-support backplane as a fixture of the CAM head by making it a component of the quick-change filter cartridge itself. This allows rapid and precise changes of precut disk-filter media without the requirement for direct contact by an operator with the filter material.

Figure 4:
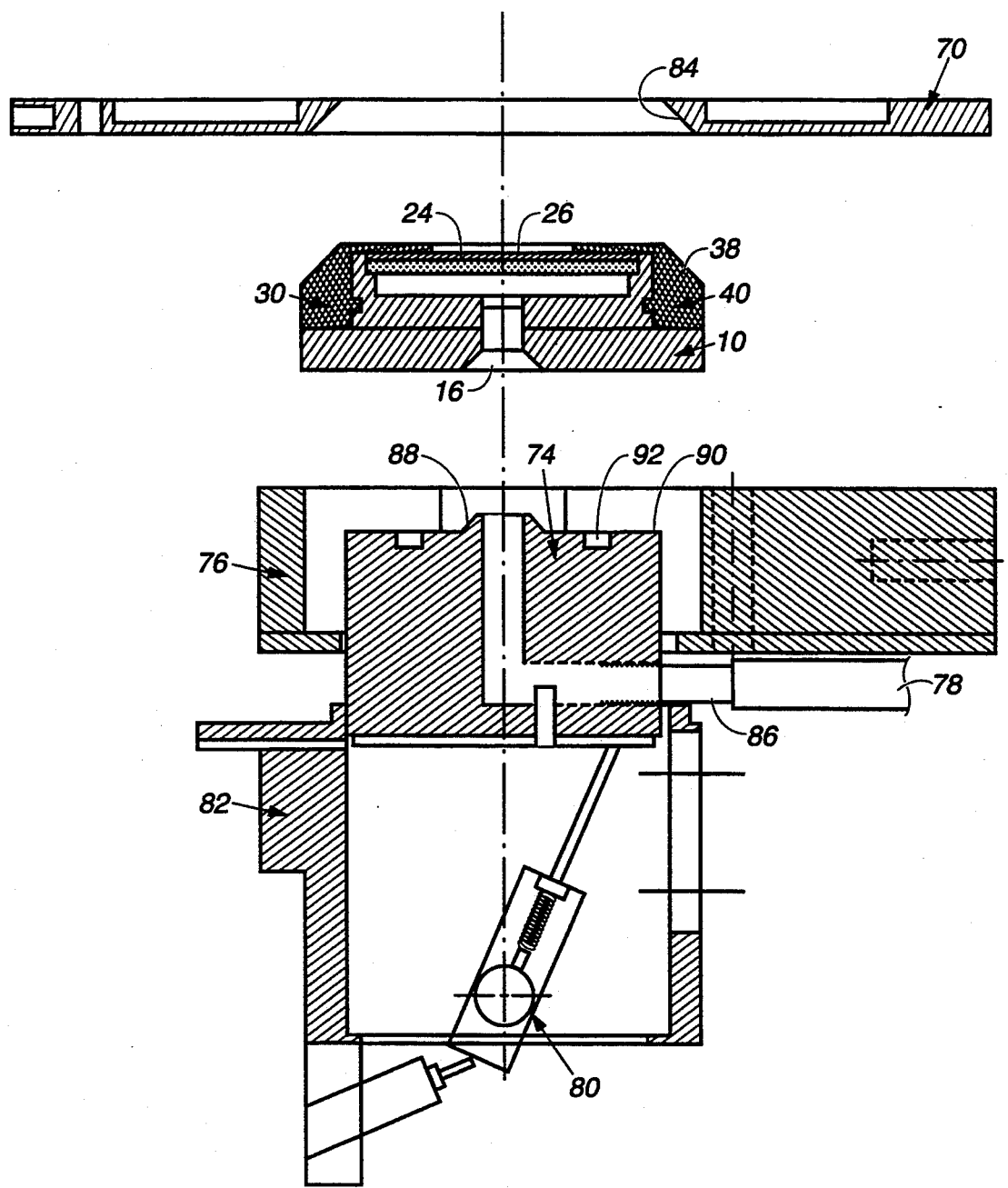
FIG. 4 is an expanded schematic representation of the manner in which the subject filter cartridge is utilized in FIG. 3 hereof.

FIG. 4, shows an expanded schematic view of the manner in which the subject filter cartridge is utilized in FIG. 3 hereof. The several components are shown in their vertical orientation, illustrating how piston 74 moving in housing 82 engages the base of filter cartridge 40 forming a vacuum seal, and then how the filter cartridge engages a tapered opening 84 in cover plate 70 which centers and positions the filter in line with, and separated by the proper distance from, the detector.

The lever and cam of the actuator 80, which provides vertical movement to the piston, are shown. The pressure from the piston compresses cap member 30 against base member 10 so that filter medium 26 is held tightly against the filter-support member 26, forming thereby a seal which resists airflow bypassing the filter medium. The external vacuum source is coupled to the filter holder through flexible hose 78 and nipple 86, through piston 74, and terminating in the conical tip 88 at the top surface 90 of the piston which mates exactly with the cone-shaped depression 16 in the base of filter cartridge 40. O-ring seal 92 on this surface seals the vacuum connection to the filter cartridge.

An FAS head design which is compatible with the filter cartridge of the present invention has been developed which would extend the benefits of the use of preloaded cartridge handling to the open face, fixed air-sampling applications as well. After sampling, the filters can be collected (without touching the filters themselves) and transferred to a laboratory vacuum-counting system where again the barcode can be read to establish a log in the data base. The count data from the CAM and FAS filters would provide an accurate quantification of activity collected which can be used to interpret the CAM record, if necessary.

The final product of such a joint sample collection and counting system will be a record of the spatial and temporal concentration of isotope-specific alpha emitters in each laboratory space being monitored. Due to the use of unique identifiers of samples and sample locations and time, the production of detailed records and summaries can be highly automated in a facility computer. All samples would be processed through the count laboratory for a detailed evaluation of each alarm.

The foregoing description of the invention has been presented for purposes of illustration and description and is not intended to be exhaustive or to limit the invention to the precise form disclosed, and obviously many modifications and variations are possible in light of the above teachings. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A filter cartridge comprising in combination:
   a. a porous, solid, short, right cylindrical filter support having a first substantially flat side upon which a filter is placed, and a second, substantially flat side, substantially parallel to said first side;

b. a base having a first axis and having a substantially planar closed end and a substantially planar open end substantially parallel thereto separated by a generally cylindrical portion, the closed end thereof having a tapered hole therethrough aligned with the axis for applying vacuum to the filter cartridge, the outside wall of the cylindrical portion of said base being adapted to receive an O-ring, and the inside wall thereof being adapted to receive said cylindrical filter support upon which the filter is placed, such that the filter support and filter are substantially perpendicular to the first axis and the filter is approximately flush with said open end of said base, said base further having a flange portion coextensive with the closed end thereof;

c. an O-ring having the appropriate dimensions to fit into the adaptation therefor in the outside wall of said base; and d. a cylindrical cap having a second axis and a first open end and a second open end and a diameter such that said cap slides over said base when the first axis and the second axis are made colinear and the second open end thereof and the open end of said base are facing each other, and said O-ring forms an airtight seal between the outside wall of said base member and the inside wall of said cap, said cap further having a circular lip reducing the diameter of the first open end thereof such that the filter is held in place against said filter support when said cap is compressed against said base.

2. The filter cartridge as described in claim 1, wherein said cap has a circular tapered portion contiguous with the circular lip and facing the outside of the first open end such that the filter cartridge may be removably located in an air sampling apparatus.

3. The filter cartridge as described in claim 1, further comprising at least one support member extending from the inside of the closed end of said base to said filter support, such that said filter support is supported away from the closed end of said base.

4. The filter cartridge as described in claim 1, further comprising a screen for covering the tapered hole in said base such that absorbing material can be introduced into the volume formed between the second flat side of said filter support and said screen in the interior of the filter cartridge.

* * * * *